(12) United States Patent
Maas et al.

(10) Patent No.: US 6,440,891 B1
(45) Date of Patent: Aug. 27, 2002

(54) CATALYST COMPRISING A COMPLEX OF A METAL OF SUBGROUP VIII, ON THE BASIS OF A PHOSPHONITE LIGAND AND METHOD FOR HYDROFORMYLATION

(75) Inventors: Heiko Maas, Schifferstadt; Rocco Paciello, Bad Dürkheim; Michael Röper, Wachenheim; Jakob Fischer, Kirchdorf; Wolfgang Siegel, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/623,175
(22) PCT Filed: Mar. 11, 1999
(86) PCT No.: PCT/EP99/01597
§ 371 (c)(1), (2), (4) Date: Aug. 29, 2000
(87) PCT Pub. No.: WO99/46044
PCT Pub. Date: Sep. 16, 1999

(30) Foreign Application Priority Data

Mar. 12, 1998 (DE) .......................... 198 10 794

(51) Int. Cl.[7] .............. B01J 31/00; C07F 9/02; C07C 27/00; C07C 45/00
(52) U.S. Cl. .................. 502/162; 558/85; 568/903; 568/454; 568/449
(58) Field of Search ................. 568/454, 451, 568/449, 903, 909.5; 502/162; 558/85

(56) References Cited

U.S. PATENT DOCUMENTS

| | | | |
|---|---|---|---|
| 4,169,861 A | 10/1979 | Hughes, I | 260/604 |
| 4,193,943 A | 3/1980 | Unruh et al. | 260/604 |
| 4,201,714 A | 5/1980 | Hughes, II | 260/340 |
| 5,312,996 A | 5/1994 | Packett | 568/454 |
| 5,360,938 A | 11/1994 | Babin et al. | 568/449 |
| 5,600,032 A | 2/1997 | Sato et al. | 568/903 |

FOREIGN PATENT DOCUMENTS

| | | |
|---|---|---|
| JP | 97/255 610 | 9/1997 |
| WO | WO 95/30680 | 11/1995 |
| WO | WO 99/13983 | 3/1999 |

OTHER PUBLICATIONS

Beller et al. "Progress in hydroformulation and carbonylation" Journal of Molecular Catalyst vol. 104 (1995) pp. 17–85.

*Primary Examiner*—Deborah C. Lambkin
(74) *Attorney, Agent, or Firm*—Keil & Weinkauf

(57) ABSTRACT

The catalyst comprises at least one bi- or more highly dentate phosphonite ligand of the general formula I

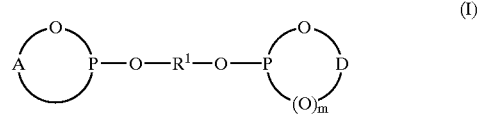

or salts and mixtures thereof and is useful in a process for hydroformylating compounds containing at least one ethylenically unsaturated double bond by reaction with carbon monoxide and hydrogen.

8 Claims, No Drawings

CATALYST COMPRISING A COMPLEX OF A METAL OF SUBGROUP VIII, ON THE BASIS OF A PHOSPHONITE LIGAND AND METHOD FOR HYDROFORMYLATION

This application is A 371 of PCT/EP99/01547 Mar. 11, 1999.

The present invention relates to a catalyst comprising a complex of a VIIIth transition group metal other than nickel with at least one bi- or more highly dentate phosphonite ligand wherein the phosphorus and one of the oxygen atoms of the phosphonite group are part of a from 5- to 8-membered heterocycle, and to a process for hydroformylating compounds containing at least one ethylenically unsaturated double bond in the presence of such a catalyst.

The hydroformylating or oxo process is widely used for the large scale production of aldehydes from olefins, carbon monoxide and hydrogen. These aldehydes may optionally be hydrogenated with hydrogen in the same operation to form the corresponding oxo alcohols. The reaction itself is highly exothermic and generally takes place under elevated pressure and temperature in the presence of catalysts. The catalysts used are cobalt, rhodium or ruthenium compounds or complexes which may be promoted with amine or phosphine ligands. Additional promoters have hitherto not achieved any significance in the industry. The hydroformylation reaction gives rise to the formation of isomeric aldehyde mixtures because of the possible CO addition to each of the two carbon atoms of a double bond. In addition, if internal olefins are used, the double bond may isomerize from an internal into a terminal position. In these isomeric mixtures, the n-aldehyde is generally favored over the iso-aldehyde, but because of the significantly greater industrial importance of the n-aldehydes it is desirable to optimize the hydroformylation catalysts with regard to achieving a greater n-selectivity.

Beller et al., Journal of Molecular Catalysis A, 104 (1995), 17–85, describe phosphine-modified rhodium catalysts for the hydroformylation of low boiling olefins. The disadvantages with these catalysts are that they can only be prepared using organometallic reagents and that the ligands used are difficult and expensive to make. In addition, these phosphine-modified catalysts are very slow to hydroformylate internal, straight-chain and branched olefins and also olefins having more than 7 carbon atoms.

WO 95/30680 describes bidentate phosphine ligands where the two phosphine groups are both bonded to an aryl radical and these two aryl radicals form a doubly bridged, ortho-fused ring system in which one of the two bridges consists of an oxygen or a sulfur atom. Rhodium complexes based on these ligands are useful as hydroformylation catalysts, and the hydroformylation of terminal olefins provides a good n/iso ratio. The disadvantage of these chelated phosphines is their difficulty of preparation, so that industrial processes which rely on such chelated phosphine catalysts are at an economic disadvantage.

U.S. Pat. No. 4,169,861 describes a process for preparing terminal aldehydes by hydroformylating α-olefins in the presence of a rhodium hydroformylation catalyst based on a bidentate ligand and a monodentate ligand. The preferred bidentate ligand is 1,1'-bis(diphenylphosphino)ferrocene. The monodentate ligand is preferably a phosphine, such as diphenylethylphosphine.

U.S. Pat. Nos. 4,201,714 and 4,193,943 have a similar disclosure content. The preparation of the bidentate phosphinoferrocene ligands requires the use of organometallic reagents, which are expensive to make, putting hydroformylation processes that employ these catalysts at an economic disadvantage.

U.S. Pat. No. 5,312,996 describes a process for preparing 1,6-hexanedial by hydroformylating butadiene in the presence of hydrogen and carbon monoxide. The hydroformylation catalysts used are rhodium complexes with polyphosphite ligands wherein the phosphorus and two of the oxygen atoms of the phosphite group are part of a 7-membered heterocycle.

JP-A 97/255 610 describes a process for preparing aldehydes by hydroformylation in the presence of rhodium catalysts comprising a monodentate phosphonite ligand.

None of the references cited above describes hydroformylation catalysts based on bi- or more highly dentate phosphonite ligands wherein the phosphonite group is part of a 5- to 8-membered heterocycle.

It is an object of the present invention to provide novel catalysts based on complexes of a metal of the VIIIth transition group. They shall be highly useful for hydroformylation and possess good catalytic activity.

We have found that this object is achieved, surprisingly, by catalysts based on complexes of a metal of the VIIIth transition group which comprise at least one bi- or more highly dentate phosphonite ligand wherein the phosphonite group is part of a from 5- to 8-membered heterocycle.

The present invention accordingly provides a catalyst comprising a complex of a VIIIth transition group metal other than nickel with a bi- or more highly dentate phosphonite ligand of the general formula I

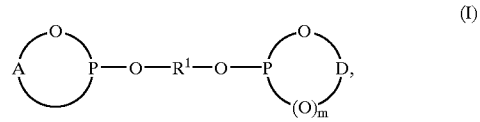

where
m is 0 or 1,

A combines with that part of the phosphonite group to which it is attached to form a 5- to 8-membered heterocycle which may optionally be additionally singly, doubly or triply fused with cycloalkyl, aryl and/or hetaryl, in which case the fused-on groups may each bear one, two or three substituents selected from the group consisting of alkyl, alkoxy, halogen, nitro, cyano and carboxyl, $R^1$ is a $C_3$- to $C_6$-alkylene bridge which may have one, two or three double bonds and/or may be singly, doubly or triply fused with aryl and/or hetaryl, in which case the aryl or hetaryl groups may bear one, two or three substituents selected from the group consisting of alkyl, cycloalkyl, aryl, alkoxy, cycloalkyloxy, aryloxy, halogen, trifluoromethyl, nitro, cyano, carboxyl and $NE^1E^2$, where $E^1$ and $E^2$ are identical or different and each is alkyl, cycloalkyl or aryl, D has the meanings specified above for A,
or salts and mixtures thereof.

For the purposes of the present invention, alkyl denotes both straight-chain and branched alkyls. Alkyl is preferably straight-chain or branched $C_1$–$C_8$-alkyl, more preferably $C_1$–$C_6$-alkyl, particularly preferably $C_1$–$C_4$-alkyl. Examples of alkyl groups are especially methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2- dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl.

Cycloalkyl is preferably $C_5$–$C_7$-cycloalkyl, such as cyclopentyl, cyclohexyl or cycloheptyl.

Substituted cycloalkyl preferably has 1, 2, 3, 4 or 5, especially 1, 2 or 3, substituents selected from the group consisting of alkyl, alkoxy and halogen.

Aryl is preferably phenyl, tolyl, xylyl, mesityl, naphthyl, anthracenyl, phenanthrenyl or naphthacenyl and especially phenyl or naphthyl.

Substituted aryl preferably has 1, 2, 3, 4 or 5, especially 1, 2 or 3, substituents selected from the group consisting of alkyl, alkoxy and halogen.

Hetaryl is preferably pyridyl, quinolinyl, acridinyl, pyridazinyl, pyrimidinyl or pyrazinyl.

Substituted hetaryl preferably has 1, 2 or 3 substituents selected from the group consisting of alkyl, alkoxy and halogen.

The above remarks concerning alkyl, cycloalkyl and aryl apply mutatis mutandis to alkoxy, cycloalkyloxy and aryloxy.

$NE^1E^2$ is preferably N,N-dimethyl, N,N-diethyl, N,N-dipropyl, N,N-diisopropyl, N,N-di-n-butyl, N,N-di-t.-butyl, N,N-dicyclohexyl or N,N-diphenyl.

Halogen is fluorine, chlorine, bromine or iodine, preferably fluorine, chlorine or bromine.

In a preferred embodiment, the present invention provides catalysts comprising at least one phosphonite ligand of the formula I wherein A combines with that part of the phosphonite group to which it is attached to form a 5- or 6-membered heterocycle which may optionally be singly or doubly fused with aryl and/or hetaryl, in which case the fused-on groups may bear one, two or three of the above-mentioned substituents.

A is then for example a 2,2'-biphenylene, 2,2'-binaphthylene or 2,3-xylylene radical which may bear 1, 2 or 3 substituents selected from the group consisting of alkyl, alkoxy and halogen. Alkyl here is preferably $C_1$–$C_4$-alkyl, especially t-butyl. Alkoxy here is preferably $C_1$–$C_4$-alkoxy and especially methoxy. Halogen is especially fluorine, chlorine or bromine.

Preferably, $R^1$ is a radical of the formula II.1, II.2, II.3 or II.4:

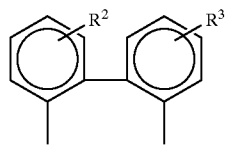

(II.1)

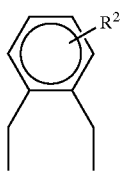

(II.2)

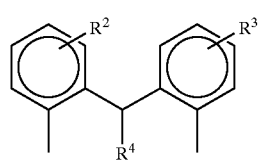

(II.3)

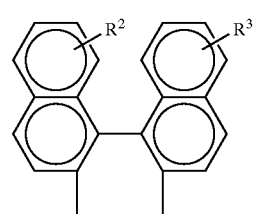

(II.4)

where $R^2$ and $R^3$ are independently hydrogen, alkyl, alkoxy, halogen, trifluoromethyl, nitro or cyano, and $R^4$ is hydrogen, alkyl, preferably methyl, or aryl, preferably phenyl, which may optionally be substituted by alkyl, alkoxy, halogen, trifluoromethyl, nitro or cyano.

The above remarks concerning preferred A apply mutatis mutandis to D.

In a suitable embodiment, the phosphonite ligands of the formula I are selected from the group consisting of ligands of the formulae Ia to Ig

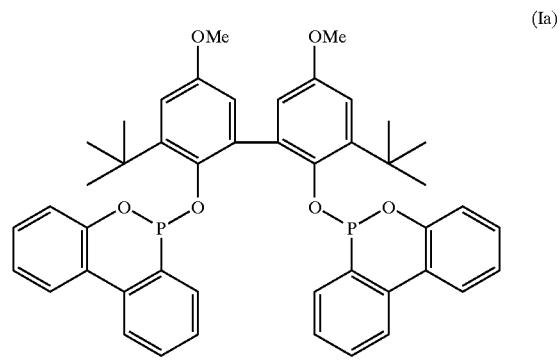

(Ia)

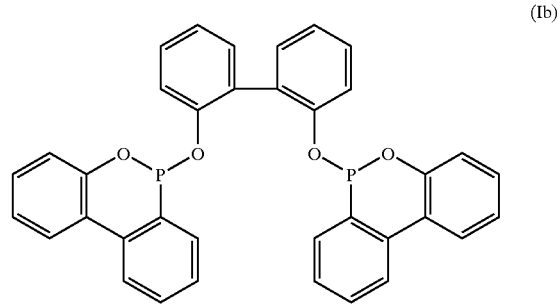

(Ib)

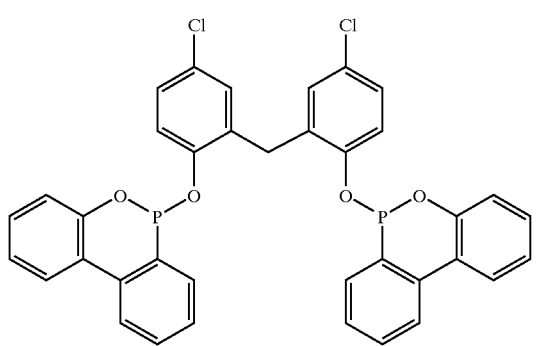

(Ic)

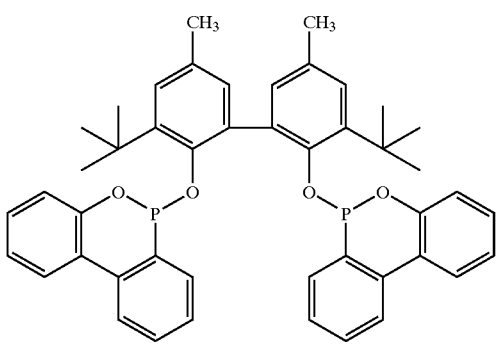 (Id)

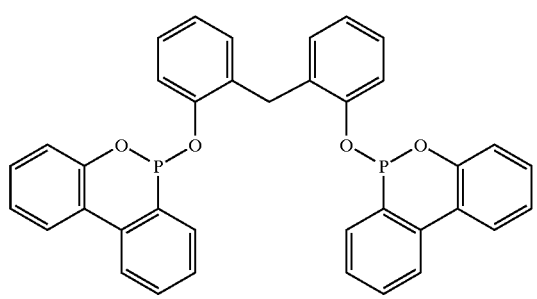 (Ie)

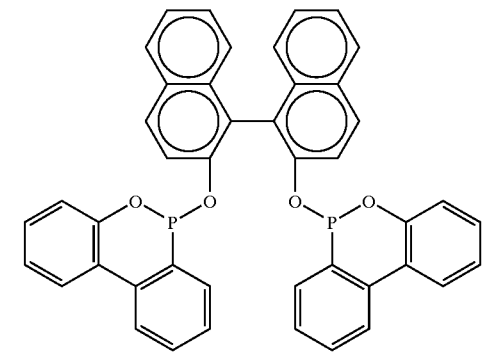 (If)

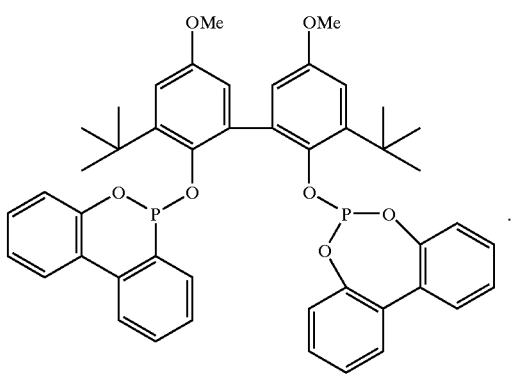 (Ig)

The catalysts of the present invention may include one or more of the phosphonite ligands of the formula I. In addition to the above-described ligands of the general formula I, they may comprise at least one further ligand selected from the group consisting of halides, amines, carboxylates, acetylacetonate, arylsulfonates, alkylsulfonates, hydride, CO, olefins, dienes, cycloolefins, nitriles, N-containing heterocycles, aromatics, heteroaromatics, ethers, $PF_3$ and phosphine, phosphinite, phosphonite and phosphite ligands, wherein the phosphine, phosphinite, phosphonite and phosphite ligands are monodentate, bidentate or polydentate. These further ligands may likewise be monodentate, bidentate or polydentate and coordinate to the metal atom of the catalyst complex. Examples of suitable further phosphorus-containing ligands are customary phosphine, phosphininte and phosphite ligands.

To prepare the phosphonite ligands of the formula I used according to the present invention, it is possible, for example, to react a hydroxyl-containing compound of the formula III with a phosphorus trihalide, preferably $PCl_3$, to form a compound of the formula IV and then to react this compound of the formula IV with a hydroxyl-containing compound of the formula $HOR^1OH$ and a compound of the formula V as per the following scheme:

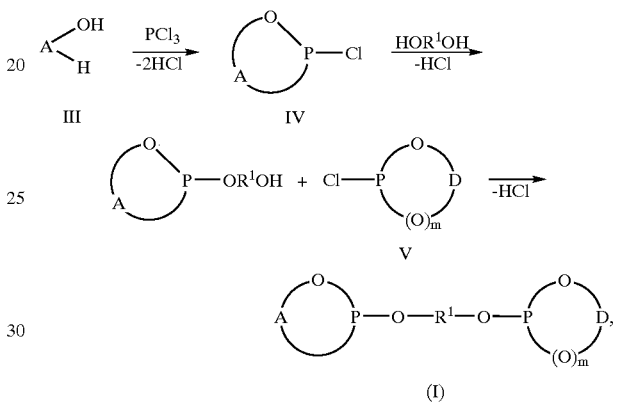

where m, A, D and $R^1$ are each as defined above. If desired, it is also possible to react 2 mol of a compound of the formula IV with ne mole of a compound $HOR^1OH$ to form a bidentate phosphonite ligand containing two identical phosphonite radicals. A process for preparing these ligands is described in Phosphorus and Sulfur, 1987, vol. 31, pages 71 ff., for the construction of 6H-dibenz[c,e][1,2] oxaphosphorine ring systems.

Suitable alcohols of the formula $HOR^1OH$ are biphenyl-2,2'-diol and binaphthyl-2,2'-diol, for example. Further suitable diols are mentioned in U.S. Pat. No. 5,312,996, col. 19, incorporated herein by reference. To prepare bidentate ligands of the formula I which bear one phosphonite and one phosphite group, it is possible to react a compound of the formula IV with a compound of the formula $HOR^1OH$ to form a monocondensation product and then to react this monocondensation product with a compound of the formula V

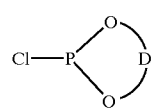

V where D has the meanings defined above for A, to form a mixed ligand of the formula I.

The compounds of the formula IV may, if desired, be isolated and subjected to purification, for example by distillation. The conversion of the compound of the formula III into a compound of the formula IV generally takes place at an elevated temperature within the range from about 40' to about 200° C., and the reaction may also be carried out by gradually increasing the temperature.

In addition, at the start of the reaction or after a certain reaction time, a Lewis acid, for example zinc chloride or aluminum chloride, may be added as catalyst. The rest of the conversion of the compounds of the formula IV into the phosphonite ligands of the formula I used according to the present invention generally takes place in the presence of a base, for example an aliphatic amine, such as diethylamine, dipropylamine, dibutylamine, trimethylamine or tripropylamine and preferably triethylamine or pyridine.

It is advantageous that it is possible to prepare the phosphonite ligands of the formula I which are used according to the present invention without recourse to organomagnesium or organolithium compounds. The simple reaction sequence provides broad scope for varying the ligands. The preparation is thus efficient and economical, from starting materials which are readily obtainable.

In general, the catalysts or catalyst precursors used in a particular case give rise under the conditions of a hydroformylation to catalytically active species of the general formula $H_xM_y(CO)_zL_q$, where M is a metal of the VIIIth transition group, L is a phosphonite ligand according to the present invention and q, x, y and z are each integers dependent on the valence and nature of the metal and the denticity of the ligand L. Preferably, z and q are independently at least 1, for example 1, 2 or 3. The sum of z and q is preferably from 2 to 5. If desired, the complexes may additionally comprise at least one of the above-described further ligands.

The metal M is preferably cobalt, ruthenium, rhodium, palladium, platinum, osmium or iridium, especially cobalt, rhodium or ruthenium.

In a preferred embodiment, the hydroformylation catalysts are prepared in situ, in the reactor used for the hydroformylation reaction. If desired, however, the catalysts of the present invention may also be prepared separately and isolated in a conventional manner. The in situ preparation of the catalysts of the present invention is effected by reacting at least one phosphonite ligand of the general formula I, a compound or a complex of a metal of the VIIIth transition group, optionally at least one further ligand, and optionally an activating agent in an inert solvent under the hydroformylation conditions.

Examples of suitable rhodium compounds or complexes are rhodium(II) and rhodium(III) salts, such as rhodium(III) chloride, rhodium(III) nitrate, rhodium(III) sulfate, potassium rhodium sulfate, rhodium(II) carboxylate, rhodium(III) carboxylate, rhodium(II) acetate, rhodium(III) acetate, rhodium(III) oxide, salts of rhodium(III) acid, triammonium hexachlororhodate(III), etc. It is also possible to use rhodium complexes, such as rhodium biscarbonylacetylacetonate, acetylacetonatobisethylenerhodium(I), etc. Preference is given to using rhodium biscarbonylacetylacetonate or rhodium acetate.

Ruthenium salts or compounds are likewise suitable. Examples of suitable ruthenium salts are ruthenium(III) chloride, ruthenium(IV) oxide, ruthenium(VI) oxide, ruthenium(VIII) oxide, alkali metal salts of ruthenium oxygen acids such as $K_2RuO_4$ or $KRuO_4$ or complexes of the general formula $RuX^1X^2L^1L^2(L^3)_n$, where $L^1$, $L^2$, $L^3$ and n are each as defined above and $X^1$ and $X^2$ each have the meanings specified above for X, for example $RuHCl(CO)(PPh_3)_3$. It is similarly possible to use the metal carbonyls of ruthenium such as trisruthenium dodecacarbonyl or hexaruthenium octadecacarbonyl, or mixed forms in which CO is partly replaced by ligands of the formula $PR_3$, such as $Ru(CO)_3(PPh_3)_2$, in the process of the present invention.

Examples of suitable cobalt compounds are cobalt(II) chloride, cobalt(II) sulfate, cobalt(II) carbonate, cobalt(II) nitrate, their amine or hydrate complexes, cobalt carboxylates, such as cobalt acetate, cobalt ethylhexanoate, cobalt naphthanoate, and also the cobalt caprolactamate complex. Here too it is possible to use the carbonyl complexes of cobalt such as dicobalt octacarbonyl, tetracobalt dodecacarbonyl and hexacobalt hexadecacarbonyl.

The compounds of cobalt, rhodium and ruthenium which have been mentioned are known in principle and have been extensively described in the literature or they can be prepared by the person skilled in the art similarly to the compounds already known.

Examples of suitable activating agents are Bronsted acids, Lewis acids, for example $BF_3$, $AlCl_3$ and $ZnCl_2$, and Lewis bases.

As solvents there are preferably used the aldehydes which are formed from the respective olefins in the course of the hydroformylation, and their comparatively high boiling consecutive reaction products, for example the products of aldol condensation. Given sufficiently hydrophilicized ligands, it is also possible to use water, alcohols, such as methanol, ethanol, n-propanol, isopropanol, n-butanol and isobutanol, ketones, such as acetone and methyl ethyl ketone, etc.

The molar ratio of phosphonite ligand of the general formula I to metal of the VIIIth transition group is generally within the range of about 1:1 to 1000:1.

The present invention further provides a process for hydroformylating compounds containing at least one ethylenically unsaturated double bond by reaction with carbon monoxide and hydrogen in the presence of at least one of the hydroformylation catalysts of the present invention.

Suitable substrates for the hydroformylation process of the present invention include in principle all compounds which contain one or more ethylenically unsaturated double bonds. These include for example olefins, such as α-olefins, internal straight-chain and internal branched olefins. Examples of suitable α-olefins are ethylene, propene, 1-butene, 1-pentene, 1-hexene, 1-heptene, 1-octene, 1-nonene, 1-decene, 1-undecene, 1-dodecene, etc.

Suitable straight-chain internal olefins are preferably $C_4$- to $C_{20}$-olefins, such as 2-butene, 2-pentene, 2-hexene, 3-hexene, 2-heptene, 3-heptene, 2-octene, 3-octene, 4-octene, etc.

Suitable branched internal olefins are preferably $C_4$- to $C_{20}$-olefins, such as 2-methyl-2-butene, 2-methyl-2-pentene, 3-methyl-2-pentene, branched internal heptene mixtures, branched internal octene mixtures, branched internal nonene mixtures, branched internal decene mixtures, branched internal undecene mixtures, branched internal dodecene mixtures, etc.

Further olefins useful for hydroformylation are $C_5$- to $C_8$-cycloalkenes, such as cyclopentene, cyclohexene, cycloheptene, cyclooctene and derivatives thereof, for example their $C_1$- to $C_{20}$-alkyl derivatives having from 1 to 5 alkyl substituents. Further olefins useful for hydroformylation are aromatic vinyl compounds, such as styrene, α-methylstyrene, 4-isobutylstyrene, etc. Further olefins useful for hydroformylation are α,β-ethylenically unsaturated mono- and/or dicarboxylic acids, their esters, monoesters and amides, such as acrylic acid, methacrylic acid, maleic acid, fumaric acid, crotonic acid, itaconic acid, methyl 3-pentenoate, methyl 4-pentenoate, methyl oleate, methyl acrylate, methyl methacrylate, unsaturated nitrites, such as 3-pentenenitrile, 4-pentenenitrile, acrylonitrile, vinyl ethers, such as vinyl methyl ether, vinyl ethyl ether, vinyl propyl ether, etc., $C_1$- to $C_{20}$-alkenols, -alkenediols and -alkadienols, such as 2,7-octadien-1-ol. Suitable substrates further include di- or polyenes having isolated or conjugated double bonds. These include for example 1,3-butadiene, 1,4-pentadiene, 1,5-hexadiene, 1,6-heptadiene, 1,7-octadiene, vinylcyclohexene, dicyclopentadiene, 1,5,9-cyclooctatriene and also butadiene homopolymers and copolymers.

The hydroformylation reaction may be carried out continuously, semicontinuously or batchwise.

Suitable reactors for the continuous reaction are known to the person skilled in the art and are described for example in Ullmanns Enzyklopädie der technischen Chemie, vol. 1, 3rd edition, 1951, pages 743 ff.

Suitable pressure-resistant reactors are likewise known to the person skilled in the art and are described for example in Ullmanns Enzyklopädie der technischen Chemie, vol. 1, 3rd edition, 1951, pages 769 ff. In general, the process of the present invention is carried out using an autoclave which, if desired, can be equipped with a stirrer and an internal lining.

The composition of the carbon monoxide/hydrogen synthesis gas used in the process of the present invention may vary within wide limits. The molar ratio of carbon monoxide to hydrogen is generally within the range from about 5:95 to 70:30, preferably within the range from about 40:60 to 60:40. Particular preference is given to using a molar ratio of carbon monoxide to hydrogen within the region of about 1:1.

The temperature of the hydroformylation reaction is generally within the range from about 20° to 180° C., preferably from about 50 to 150° C. The reaction is generally carried out at the partial pressure of the reaction gas at the reaction temperature chosen. In general, the pressure will be within the range from about 1 to 700 bar, preferably within the range from 1 to 600 bar, especially within the range from 1 to 300 bar. The reaction pressure may be varied as a function of the activity of the novel hydroformylation catalyst used. In general, the novel catalysts based on phosphonite ligands enable the reaction to take place within the region of lower pressures, for example within the range from 1 to 100 bar.

The hydroformylation catalysts of the present invention may be separated from the hydroformylation reaction effluent by customary methods known to the person skilled in the art, and can generally be reused for the hydroformylation.

The catalysts of the present invention are advantageous in being very active, so that the corresponding aldehydes are generally obtained in good yields. In addition, when used in the hydroformylation of α-olefins and of internal linear olefins they have very low selectivity with regard to the hydrogenation product of the olefin used.

Those of the above-described catalysts of the present invention which comprise chiral phosphonite ligands of the formula I are useful for enantioselective hydroformylation.

The Examples hereinbelow illustrate the invention.

EXAMPLES

A) Preparation of Ligands Ia to Ig

Example 1

Preparation of Ligand Ia 206 g (1.5 mol) of phosphorus trichloride and 204 g (1.2 mol) of 2-biphenylol are gradually heated to 50° C. and, over 8 hours, further to 140° C. while stirring in an argon atmosphere. The solution turns yellow with pronounced evolution of hydrogen chloride. After cooling to 120° C., a catalytic amount of zinc chloride (1.2 g; 17 mmol) is added, and the mixture is heated at 140° C. for 24 hours. In the course of a subsequent distillation, the reaction product 6-chloro-(6H)-dibenz[c,e][1,2]oxaphosphorine distils over at a boiling point of 132° C. (0.2 mbar). Yield: 194.8 g (69%) of white crystals; $^{31}$P NMR spectrum: δ (ppm) 134.5.

40 g (0.177 mol) of 6-chloro-(6H)-dibenz[c,e][1,2]-oxaphosphorine are introduced as an initial charge in 400 ml of toluene under argon together with 31.7 g (0.088 mol) of 4,4'-methoxy-6,6'-t-butyl-2,2'-biphenol. 20.24 g (0.2 mol) of triethylamine (dried over KOH) are added dropwise at room temperature. The mixture is then stirred at 90° C. for 120 minutes. The triethylammonium hydrochloride formed is filtered off and the filter residue is washed with tetrahydrofuran to complete the yield. The organic phases are combined and the volatiles are removed therefrom in high vacuum. The product obtained is ligand Ia in 100% crude yield. The whitish yellow solid is initially washed with n-hexane and then with diethyl ether.

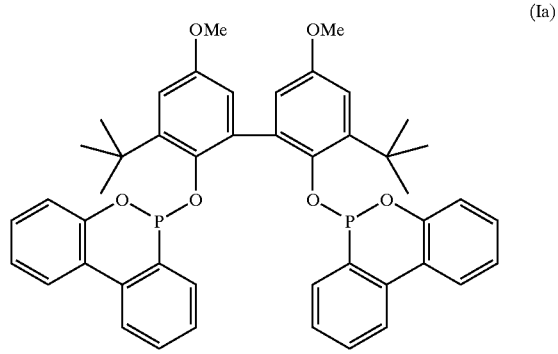

(Ia)

$^{31}$P NMR spectrum: δ (ppm) 128.14

Example 2

Preparation of Ligand Ic

Ligand Ic is prepared similarly to Example 1. The crude product obtained has a brown color and is slightly sticky. It is purified by vigorous stirring in n-hexane for 12 hours. The supernatant hexane solution is separated off to leave ligand Ic as a white powder.

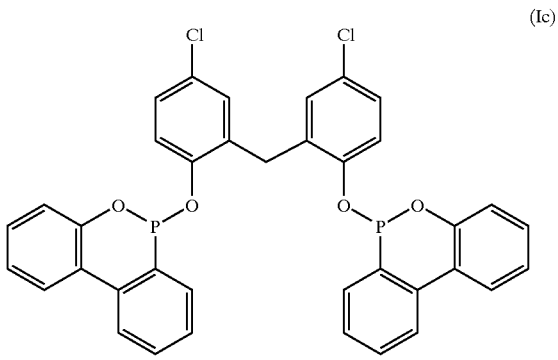

(Ic)

$^{31}$P NMR spectrum: δ (ppm) 128.41
$^1$H NMR spectrum: corresponds to proposed structure
Purity of crude product: >89%

Example 3

Preparation of Ligand If 7.95 g (33.8 mmol) of 6-chloro-(6H)-dibenz[c,e][1,2]-oxaphosphorine and 4.84 g (16.9 mmol) of 2,2'-dihydroxy-1,1'-dinaphthyl are introduced as initial charge containing 200 ml of toluene at room temperature in an argon atmosphere. At room temperature, 4.28 g (42.2 mmol) of triethylamine are added dropwise over 10 minutes. The mixture is subsequently stirred at 90° C. for one hour. The triethylammonium hydrochloride formed is filtered off and the volatiles are removed in a high vacuum to leave 11.5 g of a slightly yellowish solid (99.6% crude yield).

To remove traces of impurities, the solid is repeatedly washed with small amounts of cold methyl tert-butyl ether. The remaining solid is taken up in degassed methylene chloride. The organic solution is repeatedly extracted with degassed water, dried over sodium sulfate and concentrated to dryness to leave a white solid.

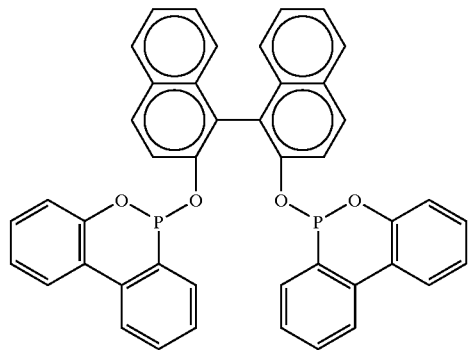

(If)

$^{31}$P NMR spectrum: δ (ppm) 131.20, 130.01, 128.75, 127.15 in a ratio of 1:1:1:1 (stereoisomers)

Purity of crude product: 97.6%

$^{1}$H NMR: corresponds to proposed structure

Example 4

Preparation of Ligand Ib

Ligand Ib was prepared similarly to Example 3 and obtained as a white solid.

$^{31}$P NMR spectrum: δ (ppm) 128.20

$^{1}$H NMR: corresponds to proposed structure

Purity of crude product: >99%

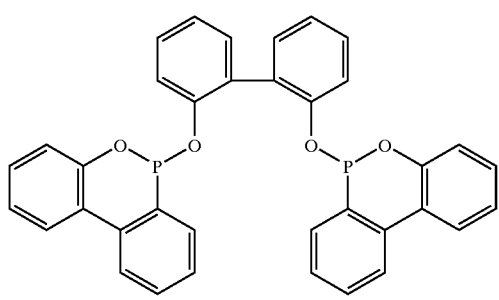

(Ib)

Example 5

Preparation of Ligand Ie

Ligand Ie was prepared similarly to Example 3 and obtained as a white solid.

$^{31}$P NMR spectrum: δ (ppm) 127.2

$^{1}$H NMR: corresponds to proposed structure

Purity of crude product: >97%

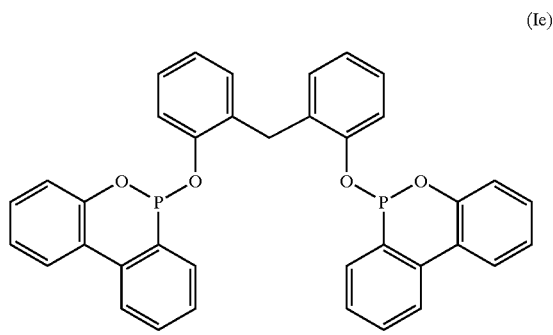

(Ie)

B) Hydroformylations

Example 6

Hydroformylation of 3-pentenenitrile

In a 10 ml steel autoclave, 0.75 mg of rhodium biscarbonylacetylacetonate, 12.3 mg of ligand If, 1.5 g of 3-pentenenitrile and 1.5 g of xylene were reacted at 100° C. with a 1:1 CO/H$_2$ synthesis gas mixture at 80 bar under argon protective gas. After a reaction time of 4 hours, the autoclave was decompressed and emptied. The mixture was analyzed by means of GC against an internal standard. The conversion was 58%. The yields were 57% of formylvaleronitrile isomers (12% of n) and 1.2% of pentanenitrile.

We claim:

1. A catalyst comprising at least one rhodium complex with a phosphonite ligand of formula I

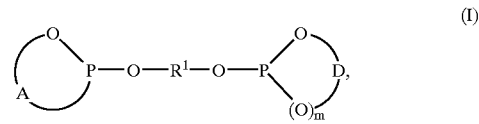

(I)

wherein

R$^1$ is a C$_3$–C$_6$-chain wherein the carbon atoms are connected through single bonds or through single bonds and from 1 to 3 double bonds, which chain is optionally fused with from 1 to 3 rings selected from the group consisting of aryl and hetaryl, wherein the rings are unsubstituted or carry from 1 to 3 substituents selected from the group consisting of alkyl, cycloalkyl, aryl, alkoxy, cycloalkyloxy, aryloxy, halogen, trifluoromethyl, nitro, cyano, carboxyl and NE$^1$E$^2$, E$^1$ and E$^2$ are identical or different and each is alkyl, cycloalkyl or aryl, m is 0 or 1, and the moieties

and

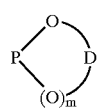

are identical or different and denote each a 5- to 8-membered heterocycle which is optionally fused with from 1 to 3 rings selected from the group consisting of cycloalkyl, aryl and hetaryl, wherein the rings are unsubstituted or carry from 1 to 3 substituents selected from the group consisting of alkyl, alkoxy, halogen, nitro, cyano and carboxyl, or a salt thereof.

2. The catalyst defined in claim 1, wherein A or D represents a biradical selected from the group consisting of 2,2'-biphenylene, 2,2'-binaphthylene and 2,3-xylylene, wherein the biradical is unsubstituted or carries from 1 to 3 substituents selected from the group consisting of alkyl, alkoxy and halogen.

3. The catalyst defined in claim 1, wherein $R^1$ is a radical of formula II.1, II.2, II.3 or II.4

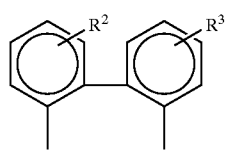
(II.1)

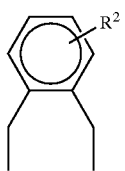
(II.2)

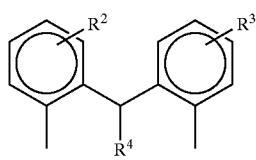
(II.3)

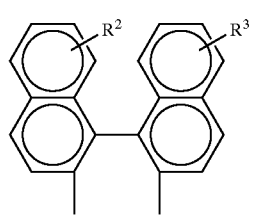
(II.4)

wherein
$R^2$ and $R^3$ are independently hydrogen, alkyl, alkoxy, halogen, trifluoromethyl, nitro or cyano, and
$R^4$ is hydrogen or alkyl, or is aryl, which is unsubstituted or substituted by alkyl, alkoxy, halogen, trifluoromethyl, nitro or cyano.

4. The catalyst defined in claim 2, wherein $R^4$ is hydrogen or methyl, or is phenyl, which is unsubstituted or substituted by alkyl, alkoxy, halogen, trifluoromethyl, nitro or cyano.

5. The catalyst defined in claim 1, wherein the phosphonite ligand is selected from the group consisting of ligands of formulae Ia to Ig

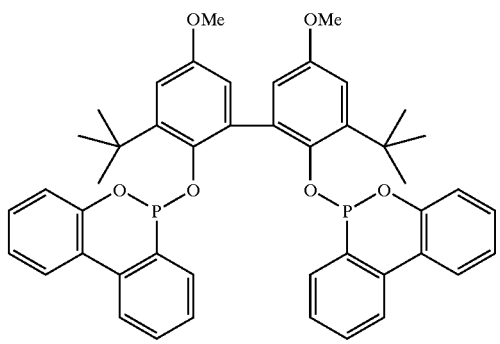
(Ia)

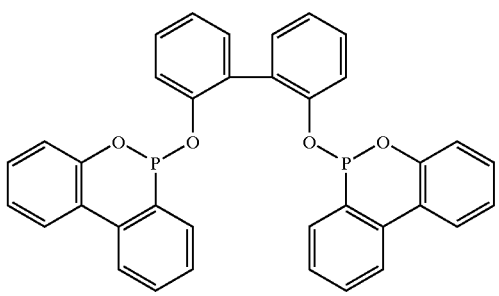
(Ib)

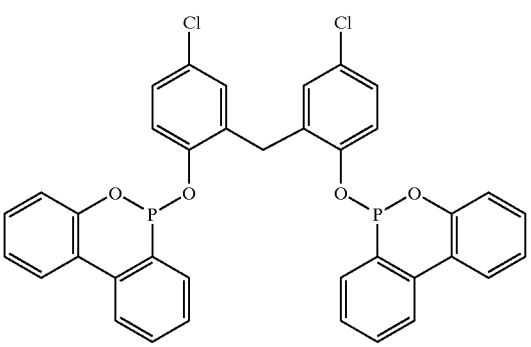
(Ic)

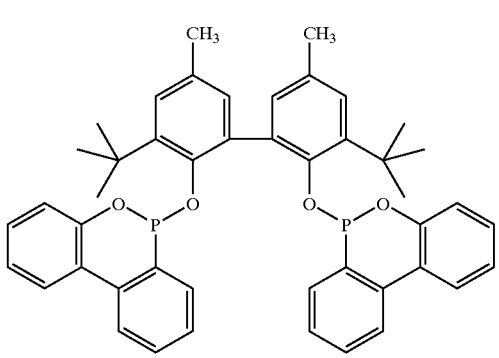
(Id)

(Ie)

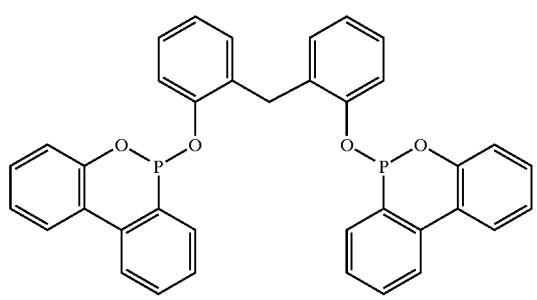

(Ig)

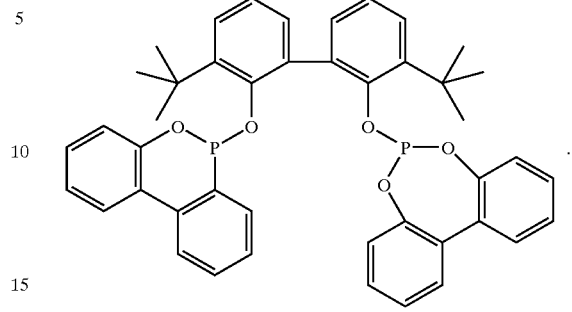

(If)

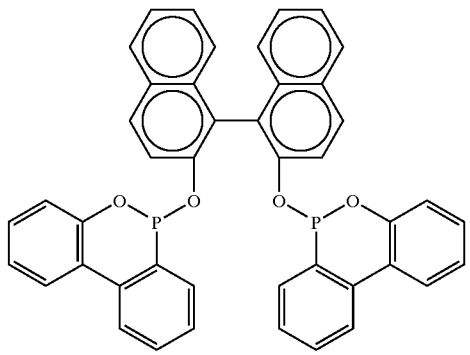

6. The catalyst defined in claim 1, further comprising at least one additional ligand selected from the group consisting of halides, amines, carboxylates, acetylacetonate, arylsulfonates, alkylsulfonates, hydride, CO, olefins, dienes, cycloolefins, nitriles, N-containing heterocycles, aromatics, heteroaromatics, ethers, $PF_3$, phosphine, phosphinite and phosphite ligands, wherein the phosphine, phosphinite and phosphite ligands are monodentate, bidentate or polydentate.

7. A process for hydroformylating compounds containing at least one ethylenically unsaturated double bond by reacting said compounds with carbon monoxide and water in the presence of a hydroformylation catalyst, wherein the hydroformylation catalyst is the catalyst defined in claim 1.

8. The process of claim 7, wherein the catalyst is prepared in situ by reacting at least one phosphonite ligand of formula I, a compound or a complex of a metal of the VIIIth transition group and optionally an activating agent in an inert solvent under the hydroformylation conditions.

* * * * *